United States Patent [19]

Selby

[11] 4,445,365

[45] May 1, 1984

[54] TAPERED BEARING SIMULATOR-VISCOMETER

[76] Inventor: Theodore W. Selby, 234 E. Larkin St., Midland, Mich. 48640

[21] Appl. No.: 378,835

[22] Filed: May 17, 1982

[51] Int. Cl.³ .......................................... G01N 11/14
[52] U.S. Cl. ...................................................... 73/60
[58] Field of Search .............................................. 73/60

[56] References Cited

U.S. PATENT DOCUMENTS

| 2,027,903 | 1/1936 | Dintilhac | 73/60 |
| 2,305,531 | 12/1942 | Hurndall | 73/60 |
| 2,807,160 | 9/1957 | Asbeck | 73/60 |
| 2,907,563 | 10/1959 | Verde et al. | 73/60 X |
| 3,350,922 | 11/1967 | Kim et al. | 73/60 |
| 3,456,494 | 7/1969 | Zimmer | 73/60 |
| 4,077,251 | 3/1978 | Winter | 73/59 |

FOREIGN PATENT DOCUMENTS 1025743  4/1966  United Kingdom ..................... 73/60

OTHER PUBLICATIONS

E. M. Barber et al., "A High Rate of Shear Rotational Viscometer", Analytical Chemistry 27, 425–429 (1955).
W. C. Pike et al., "A Simple High Shear Viscometer" etc. Soc. Auto. Engineers (SAE), Publ. 780981 (1978), Reprinted at SAE-SP-343, at p. 47ff.
R. M. Stewart et al., "Proposed Laboratory Methods for Predicting the Low Temperature Pumpability Properties of Crankcase Oils" SAE Publ. 730479 (1973).

Primary Examiner—Gerald Goldberg
Assistant Examiner—Joseph W. Roskos
Attorney, Agent, or Firm—William Miller Yates

[57] ABSTRACT

A rotational viscometer or tapered bearing simulator for testing motor oils and other fluids has a stator, a matching rotor fitting into it, and a drive shaft extending axially from the rotor. The shaft is direct-driven by a multispeed synchronous AC motor mounted on a low-friction turntable free to rotate over a limited arc. Torque experienced by the turntable is measured by a strain gage. The turntable rests on a platform which is vertically adjustable by and cantilevered from a fine screw-equipped elevator bracket. For temperature control, the stator is embedded in thermally insulating material and surrounded by an electric heating coil and a passageway through which air may flow. The stator and rotor have closely matched parallel surfaces produced by fine grinding. The rotor may have flats modified with a small fillet to entrap any minute particles in the test fluid. A pre-load assembly including weights applies measured torque to the turntable to calibrate and help stabilize the instrument.

15 Claims, 12 Drawing Figures

U.S. Patent  May 1, 1984  Sheet 3 of 3  4,445,365
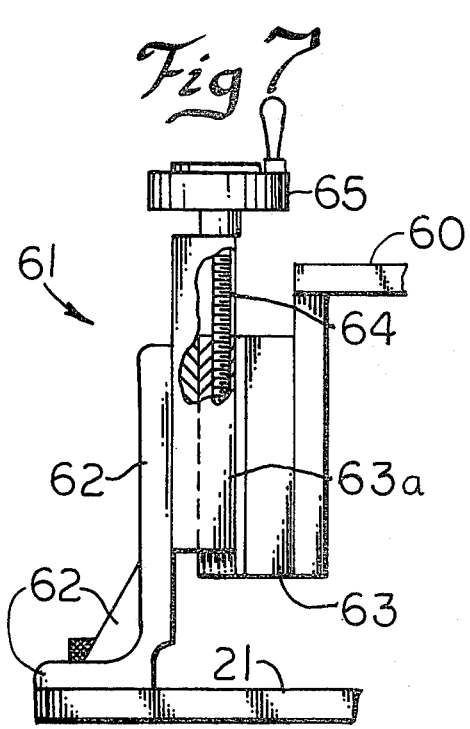
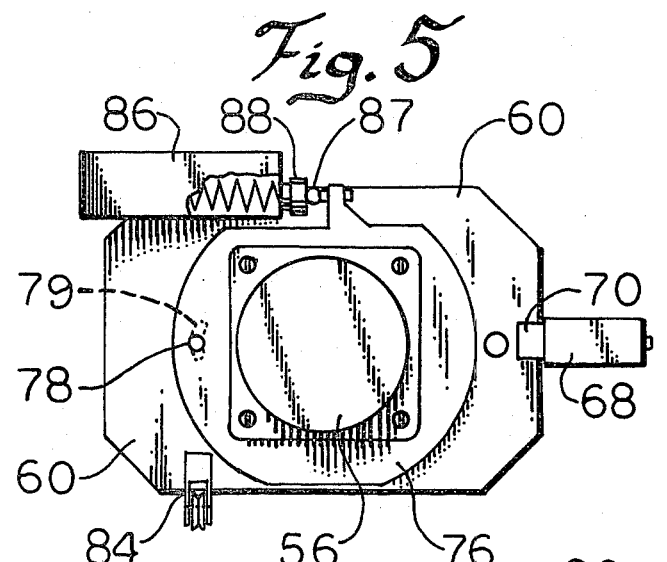
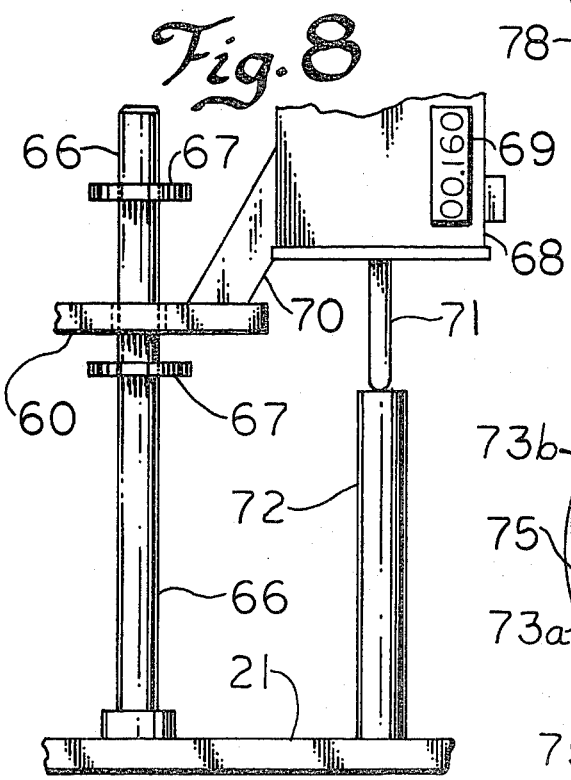
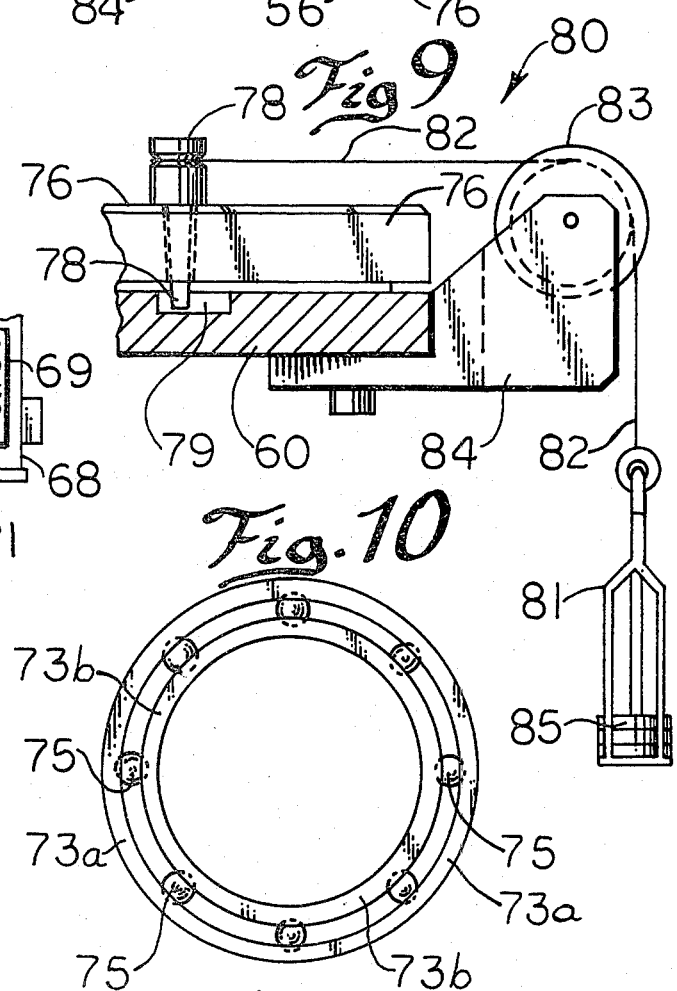

TAPERED BEARING SIMULATOR-VISCOMETER

FIELD OF THE INVENTION

This invention relates to an instrument for measuring the flow properties of fluids. It particularly concerns improvements in a rotational viscometer of tapered rotor/stator geometry for testing lubricating oils and other liquids at high shear in a shearing environment similar to that of a journal bearing.

PRIOR ART

In the automotive industry, it is important to be able to determine and predict viscosity and performance characteristics of an engine oil and other liquid lubricants without having to test them in an actual engine or other mechanism running under laboratory conditions. To this end, several rotational viscometers have been developed. (See, for example, U.S. Pat. No. 3,350,922 and an article by W. C. Pike et al, SAE Paper No. 780981 [1978].) They are intended, among other things, for studying non-Newtonian fluids such as multigrade motor oils formulated by blending viscosity index improvers, synthetic polymers, into straight mineral oils.

These known instruments, though useful, have for the most part been complex, expensive, sometimes unstable, and reliable only in the hands of qualified scientists.

SUMMARY OF THE INVENTION

The present invention has as its main object to provide an improved rotational viscometer which is sturdy, stable, relatively inexpensive, and reliable with an operator of ordinary skill. A related object is to provide a variable-gap viscometer allowing operation at precisely controlled temperatures at high shear rates up to and beyond one million reciprocal seconds.

The new instrument, in common with known rotational viscometers, has a stator, rotor, and drive shaft extending axially from the rotor. The stator is a block with a sample-receiving bore, cylindrical or inverted frustoconical with very slight taper. The rotor matches and extends axially into the bore to define therebetween a thin annular gap in which the sample being tested undergoes shear as the rotor is turned. The amount of resistance to shear developed under predetermined conditions provides a measurement of the viscometric properties of the sample.

In the present invention, the rotor shaft is direct-driven, by a comparatively small motor coaxial with it, preferably a multispeed synchronous AC motor. This motor is mounted on a low-friction turntable which is free to rotate over a limited arc. As the motor turns the rotor shaft, the motor housing experiences torque reflective of drag on the rotor by the sample in the measuring gap. The torque is transmitted to the turntable, tending to rotate it. Opposing and restraining such rotation is a stationary measuring element or strain gauge which balances out the torque and gives an output indicative of it. This output, transmitted electronically to a meter or recorder, is the ultimate measurement produced by the instrument.

The turntable rests on a platform which, in the case of a tapered rotor/stator pair, is made vertically adjustable by a fine elevator screw, to control the dimension of the gap between the stator and rotor. The platform may be made with only a single support, cantilevered from the elevator.

For temperature control, the stator is embedded in thermally insulating material and is surrounded by temperature control means. The temperature of the sample being tested is measured by a sensing element inserted in the stator and connected to an indicator-controller adapted to energize the control means.

Further refinements in the invention, hereinafter described, deal with the surface finish of the stator and rotor, with a special configuration of the rotor to offset the effect of minute particles in the test sample, and a pre-load assembly for stabilizing and helping calibrate the instrument.

BRIEF DESCRIPTION OF THE DRAWINGS

The invention may be explained with reference to the drawings, in which

FIG. 5 is a complementary top view of the upper part of the instrument, showing the motor platform and associated parts, the baseplate, test cell and weight cage having been removed;

FIG. 7 is a fragmentary front view, partly cutaway, showing the elevator assembly;

FIG. 8 is a fragmentary front view, showing the micrometer assembly;

FIG. 9 is a fragmentary side view, showing the pre-load assembly;

FIG. 10 is a top view of the turntable bearing;

FIG. 11 is a front view of the instrument panel; and

DESCRIPTION OF THE PREFERRED EMBODIMENT

Figure 1:
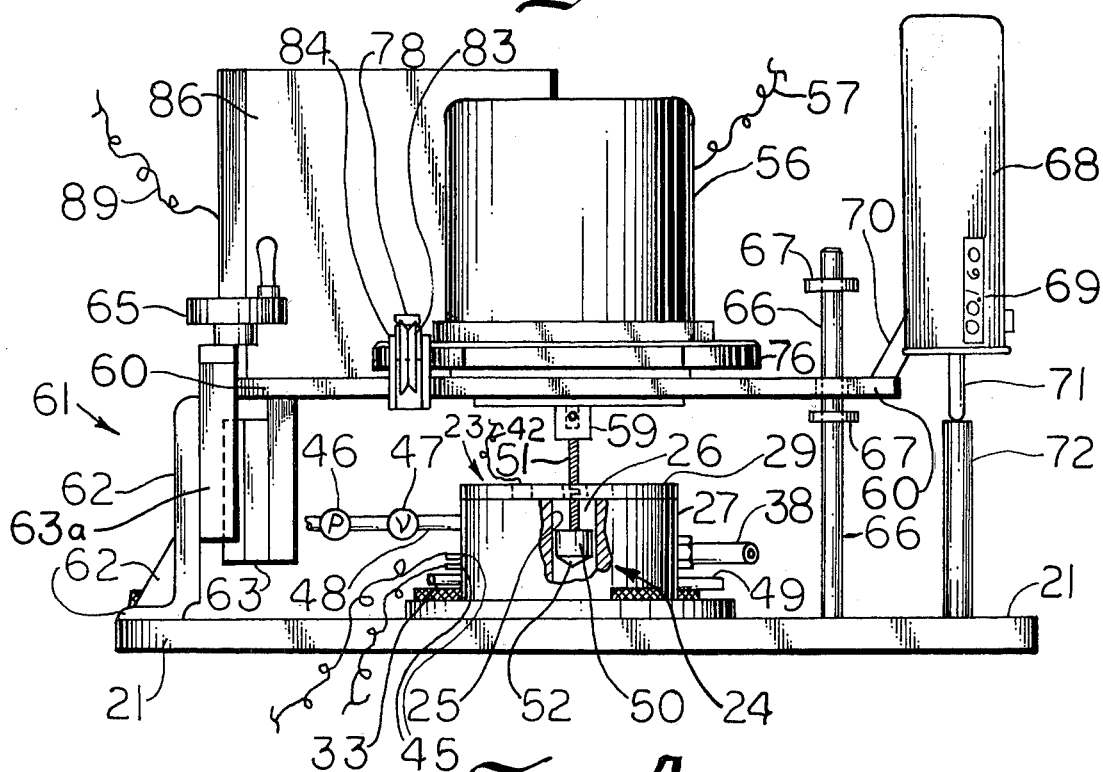
FIG. 1 is a front view, partly cutaway, of a preferred form of the instrument of the invention, illustrating generally the interrelation of the operating parts, with the weight cage removed.

The working parts of the viscometer are supported on a single base plate 21 (FIG. 1) to make a portable unit. Electronic readout and controls are on a separate instrument panel 22 (FIG. 11).

Figure 4:
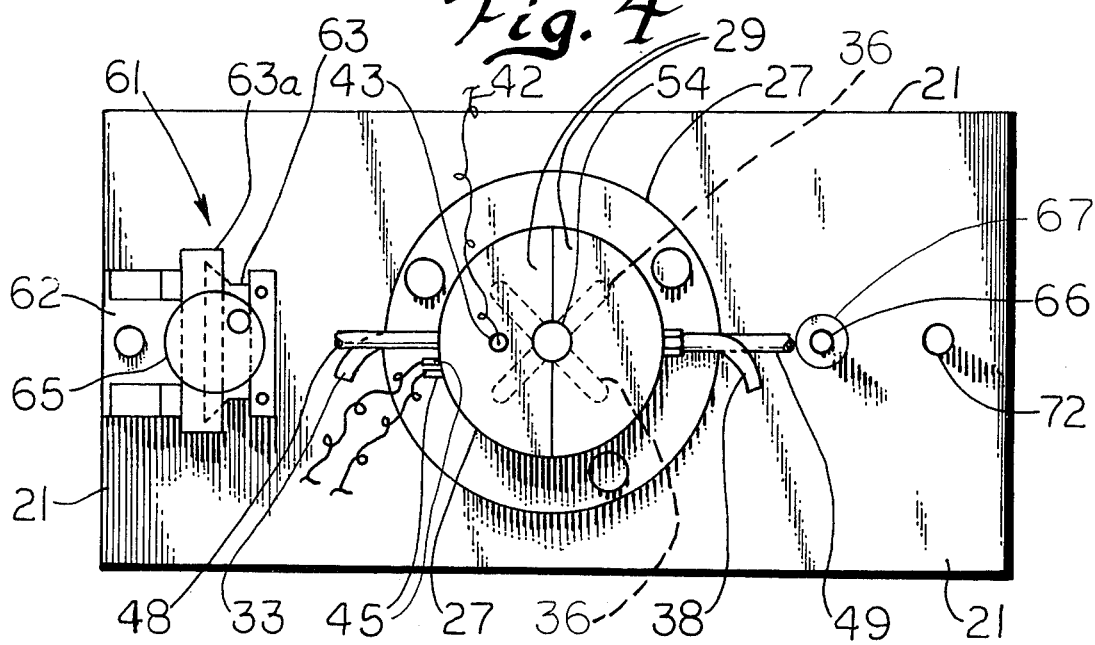
FIG. 4 is a top view of the lower part of the instrument, showing the test cell housing the baseplate, the motor platform and associated parts having been removed.

The viscometric test cell, indicated generally as 23 (FIG. 1), comprises a cup-like stator block 24 having a vertical sample-receiving bore or well 25 and a rotor 26 matching the bore and extending into it. The stator is made of copper or other thermally-conductive material, while the rotor can be made of any dimensionally stable material, e.g. stainless steel. The annular space between the two forms a gap in which the fluid being tested is subjected to rotational shear. Surrounding the stator block and supporting it is a housing 27 held adjustably on the base plate by thumbscrews. The housing is made of polytetrafluoroethylene or other thermally-insulating material and defines a cylindrical stepped cavity 28 into which the stator block 24 and associated elements fit. It is closed at the top by a two-piece over 29 (FIG. 4).

Figure 2:
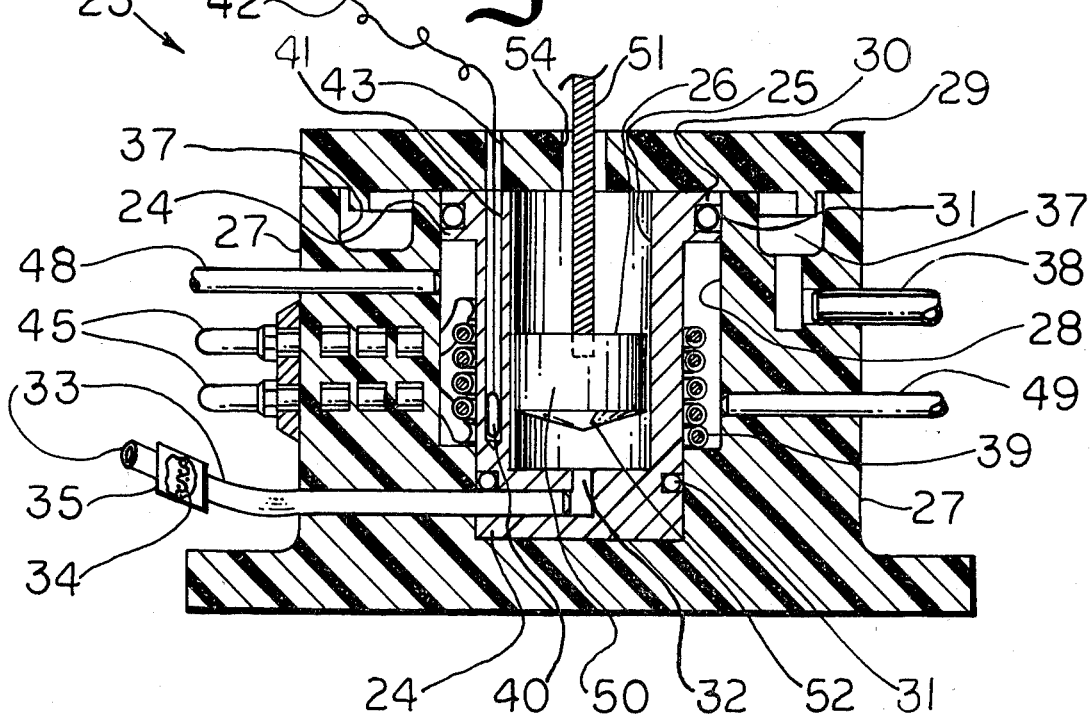
FIG. 2 is an enlarged vertical axial section through the test cell of the instrument.

The stator block is generally cylindrical, with a flange 30 at the top (see FIG. 2). It is held fluid-tight in the housing by O-rings 31. The bore 25 of the stator is circular in cross-section and tapers inwardly from the top down, being thus inverted frustoconical in shape. The degree of taper is slight, preferably 1:160. In a convenient size, the stator is about 62 mm. long, 30 mm. outside diameter below the flange, and 18 mm. inside diameter. At the bottom, and extending axially into the bore is a sample inlet 32 fed through a fill-tube 33 which enters radially through the housing. Fluid to be tested is introduced here, preferably passing first through a fine-mesh screen 34 in a filter cartridge 35 fitted to the fill-tube. Any excess fluid overflows the stator well through radial grooves 36 in the underside of the cover 29 leading to an annular groove 37 in the housing emptying into an outlet 38 connected to a drain or used for recirculation.

During high temperature viscosity measurements, the stator block 24 is heated by an insulated coil 39 of electric resistance wire surrounding it within the cavity 28 of the housing. For control, an electrical resistance thermometer 40 is seated in a sensing well 41 in the block, with leads 42 running through an opening 43 in the cover to an electronic temperature indicator-controller 44 of conventional design (FIG. 11). This latter is connected to increase the electric current flowing to the coil 39 by way of terminals 45 (FIG. 2) whenever the temperature of the block falls below a predetermined value set on the controller. The controller 44 is preferably one affording proportional rather than off-on control. For tempering the heating effect of the coil, or for cooling, a small stream of air from a pump 46 and valve 47 may be passed through the housing cavity 28 by way of an inlet 48 and outlet 49.

Figure 6:
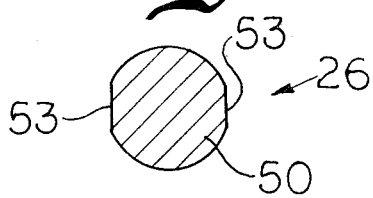
FIG. 6 is a horizontal section through the drum portion of the rotor, showing the flats.

The rotor (FIG. 2) comprises a relatively massive bob or drum 50, which is slightly frustoconical, tapered to the same degree as the stator bore so as to match and fit into it with precision, to form therebetween the thin annular viscosity-measuring gap. At its lower end the drum has a shallow conical tip 52 to eliminate the migration and trapping of air bubbles in the gap during measurement. To fit the preferred stator above, the drum is about 18 mm. in diameter and 13 mm. long, the tip extending another 2.5 mm. As shown in FIG. 6, the drum 50 is made with a pair of symmetrical flats 53 on its periphery, to achieve the configuration and advantages explained in U.S. Pat. No. 3,350,922.

Axially within the drum and fixed to it is a flexible drive shaft 51 or cable which extends upwardly through a hole 54 in the cell cover 9. The shaft is turned by a small two-speed synchronous AC motor 56. The motor rotates clockwise (as seen from above), receiving its power through leads 57 from switches 58 on the instrument panel. The rotor 26, the flexible shaft 51, and the motor 56 are all coaxial, interconnected by a coupling 59. For the preferred test cell above, the motor is a commercial model for 120 v. 50/60 Hz. current, operable at 1500/1800 and 3000/3600 rpm, and rated 1/50 hp. (15 w.) and 1/25 hp., respectively.

The motor and associated parts rest on a platform 60 (FIG. 1) adjustable by an elevator mechanism indicated generally at 61. This assembly is borne by a vertical bracket 62 bolted to the base plate 21. The elevator includes a slide plate 63 moving up and down in grooves in a retainer 63a. Vertical position may be set with precision by a fine screw 64 turned by a handwheel 65. The platform 60 is bolted to and cantilevered from the slide plate 63 as its only support. At the opposite side, a shaft 66 extends up from the base plate, passing loosely through a hole in the platform. This shaft and stop collars 67 on its limit travel of the platform and protect it against gross movement but otherwise do not touch it.

As will be appreciated, raising or lowering the platform 60 by means of the fine screw 64 causes the viscometer rotor 26 to move out of or into the stator cell 25, enlarging or narrowing the gap between the two. With the taper of 1:160 mentioned above, movement of the platform by 160 units of length changes the width of the measuring gap by one unit. For precise measurement of this gap, a micrometer 68 with digital indicator 69 reading in 0.001 mm. units, is mounted on an arm 70 extending from the platform 60 (See FIG. 8). The probe 71 or sensor of the micrometer bears against the top of a pedestal 72 seated on the base plate 21. Zeroing of the micrometer may be accomplished by adjustments not shown.

Inset into a large circular opening through the platform 60 is a turntable assembly which supports the motor 56 and allows the motor housing to rotate within a limited arc. (See FIGS. 1, 3, 5, 9, and 10.) The motor rests on and is bolted to a turntable 76 or torque ring, with the arbor of the motor extending downwardly through a central opening in the table to couple with the flexible shaft 51. Supporting the turntable 76 and socketed in the platform 60 is a ball bearing including concentric outer and inner race rings 73a and 73b with balls 75 between. The outer race ring 73a seats on a peripheral shoulder 74 around the opening in the platform. The inner race ring 73b supports the turntable 76, which is made with peripheral shoulder 77 or retainer to rest on the race ring. Retainers or covers not shown protect the bearing from dirt. This assembly, it will be appreciated, leaves the turntable and motor housing free to rotate smoothly and at very low friction. This rotation is limited to a small arc by a removable stop post 78 which rests in a hole in the turntable and extends down into a slot 79 in the platform 60. The slot is sized to allow the turntable to rotate through a few degrees of arc.

A pre-load assembly (generally 80) applies predetermined torque to the turntable in the direction opposite to that in which the motor turns. The assembly includes a weight cage 81 hanging from a cord or line 82 which goes over a pulley 83 and is looped around the stop post 78 (FIG. 9). The pulley is held at the end of a bracket 84 on the motor platform extending out beyond its edge. Disk weights 85 of calibrated value fit into the cage, imposing a pull of known magnitude on the cord. This pull is transmitted by the stop post 78 to the turntable 76 as torque. For a test cell of the preferred dimensions above, the cage 81 and weights 85 are conveniently 10.0 g. each.

Figure 3:
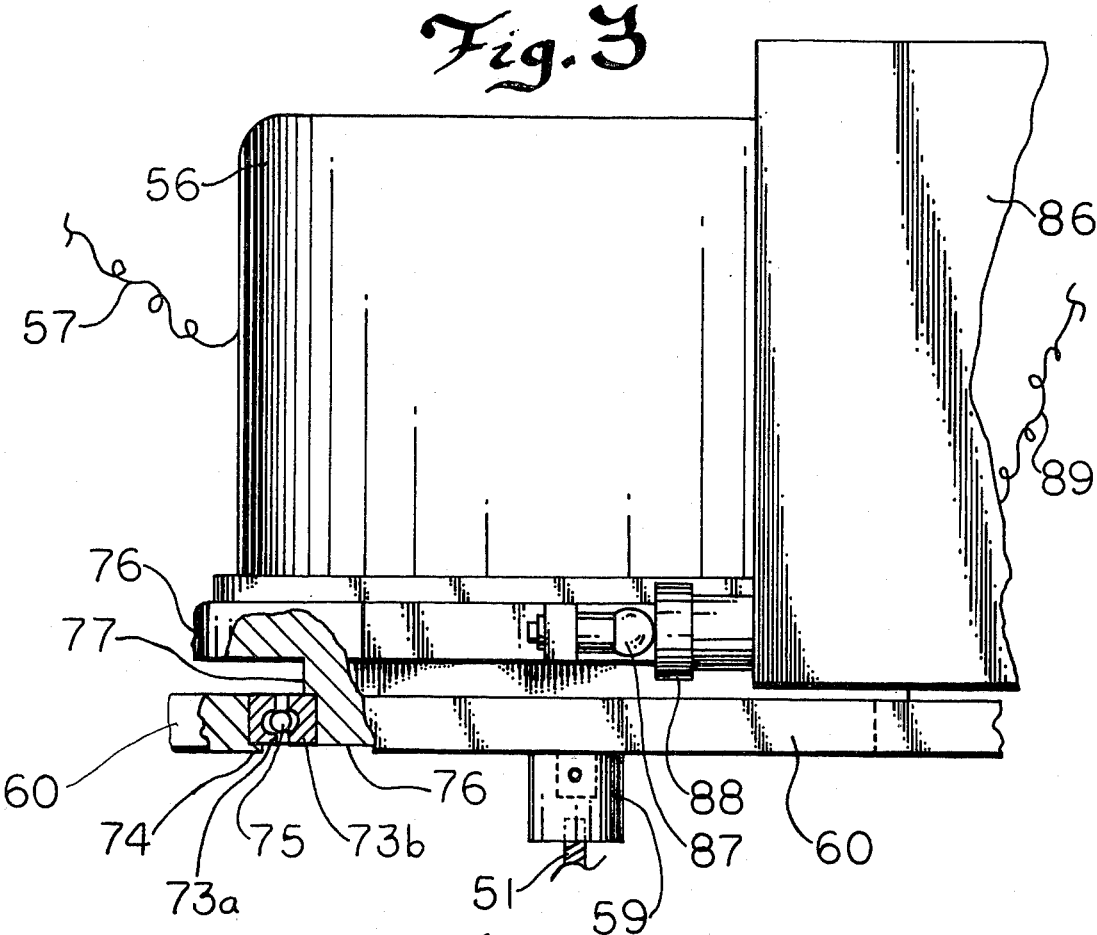
FIG. 3 is a fragmentary rear view, partly in vertical axial section, showing the motor, turntable, load cell, and support platform.

The torque on the turntable is measured by a load cell 86 mounted on the motor platform 60 just outside the periphery of the turntable (FIGS. 3 and 5). A torque arm or load ball 87 is secured to the turntable and projects radially therefrom in position to bear against the anvil 88 of the load cell as the turntable tends to move along the arc within which it is free to turn. The load cell thus opposes the rotation of the turntable and gives an output indicative of the torque required to balance out and restrain the tendency toward rotation. The load cell 86 is a force-measuring unit, conveniently a standard electronic strain gage, and is connected by leads 89 to a conventional digital voltmeter 90 on the instrument panel. Alternatively, torque readout may be made by a strip chart recorder, not shown, or other measuring device.

As already stated, the various sensing and control elements of the instrument are all connected electrically by leads to the instrument panel 22 (FIG. 11). Toward the left of the panel is the temperature indicator and control unit 44 displaying in degrees centigrade. Next is the torque readout meter 90, in volts, or, with a micro processor, in units of viscosity. At the right are off-on and high-low switches 58 for motor power and speed, and an off-on power switch 91 for the entire instrument. Included in the meters, but not shown, are standard elements providing fine adjustment and zeroing and allowing pre-setting of the temperature control point.

Having thus explained the construction of the new instrument in a preferred form, its operation will now be described.

Prior to beginning viscometric tests, the load cell 86 and its torque readout meter 90 are calibrated by use of the pre-load assembly 80. The rotor 26 is uncoupled to let the motor run free during this calibration. The turntable 76 is moved by hand enough to disengage contact between the load ball 87 and the load cell anvil 88. With the instrument and motor power on, the torque readout 90 in volts is zeroed with the motor at its lower speed (1800 rpm). The weight cage 81 is then suspended from the pulley 83 and the cord 82 is looped over the stop post 78. Its weight (10.0 g.) moves the load ball into contact with the anvil and produces a torque reading on the voltmeter 90 which is recorded. Additional weights (10.0 g. each) are added to the cage one by one, and the torque in each instance is noted. The successive readings may be graphed to provide a calibration curve (volts per gram) for the load cell.

Next, after reattaching the rotor/motor coupling 59, the stator 25 and matching rotor 26 are calibrated by operating the viscometer with a series of Newtonian reference oils of known viscosity characteristics. For purposes of such calibration it should be noted that at a known rotational speed, a liquid of known viscosity will impose a calculable torque on a rotor of known dimensions from which can be calculated both the gap between the rotor and the stator and the shear rate which the liquid is experiencing according to the equation $$FhR = \eta A V r$$

in which 'F' is the force in dynes measured by the torque-meter, 'h' is the gap in centimeters between the rotor and stator, 'R' is the distance in centimeters from the axis of rotation to the point of the ball contact on the anvil, '$\eta$' is the viscosity in poises at the temperature of operation, 'A' is the effective shearing surface area in square centimeters of the rotor (corrected for the flatted or incised areas), 'V' is the rotor surface velocity in centimeters per second, and 'r' is the rotor radius in centimeters. To determine the shear rate (usually carrying the dimensions of reciprocal seconds, 1/sec., or [cm/sec]/cm), the above equation is transposed as follows:

$$\text{Shear Rate} = V/h = (F/A)(R/r)/\eta.$$

The usually preferred gap for testing is that at which the instrument achieves a shear rate of one million reciprocal seconds ($10^6$ sec$^{-1}$). At this value, the mean thickness of the oil film between the rotor and stator is about three to four microns.

In making the calibration, the stator bore 25 is first filled to overflowing with oil by injecting the liquid through the fill tube 33. The rotor 26 is put in place in the bore and lowered carefully while turning the flexible shaft motor connector 59 slowly by hand until the rotor just begins to drag as it comes into close proximity to the stator. At this point the micrometer 68 is zeroed after which the rotor is raised by 500 microns. The test cell 23 is then brought up to the desired operating temperature preferably in an incremental fashion by raising the indicator-controller 44 set point about 25° C. at a time, energizing the heating coil and resetting the indicator-controller in 25° C. increments after 15° to 20° C. of each 25° C. increment has been reached until the desired temperature is attained. (Alternatively, a viscous fluid of about 100 centipoise at room temperature may be injected into the cell. The test cell is brought to 50° C. incrementally after which the motor is switched on at highest speed and the heat generated by the shearing of the viscous liquid used to assist in heating the test cell.)

When the test cell is at the preselected test temperature, a liquid of known viscosity at the test temperature is injected into the cell while the motor is turning the rotor and the test cell is allowed to again come to thermal equilibrium. The rotor/stator gap is then set to produce the desired shear rate by using the equation above with the known or desired values of Shear Rate, 'A', 'R', 'r', and '$\eta$' to determine the necessary 'F' in grams and thence in volts from the grams/volts calibration described above. In practice, the rotor is lowered or raised by operating the elevator 61 to produce the desired voltage readout on the torque meter 90.

Once the shear rate desired has been established by the foregoing procedure, the remaining reference fluids are injected in sequence through the fill tube, brought to temperature equilibrium, and each is recorded as to its torque readout voltage. The results from this set of liquids provide the calibration for the instrument and, over a viscosity range up to at least 17 centipoise, show a reasonably linear relationship between viscosity and the output voltage from the torquemeter. Changes in shear rate can be effected by either changing the speed of the motor or by changing the width of the gap by raising or lowering the rotor within the stator using the precision micrometer to set the desired gap.

When calibration is thus completed, unknown samples may be tested for their viscometric properties. Each sample to be tested is injected through the fill tube 33 with each entering liquid sample displacing the previous test liquid which overflows to the drain tube 38. To apply a shear rate of one million reciprocal seconds, a test cell of the preferred size works best with fluids having viscosities less than thirty centipoises.

Care should be taken in use of the instrument to avoid jamming the rotor and stator together and possibly scoring them. When the rotor is turning, hydrodynamic forces generated by the rotor on the fluid in the gap keep the rotor coaxially self-aligned relative to the stator; the gap tends to stay uniform in width around its periphery. As is known, the flats 53 on the rotor enhance this stabilizing action.

In operating the instrument with a narrow test gap on oils of relatively high viscosity, substantial heat is generated in the test fluid undergoing shear. This heat is absorbed in the stator block 24. Under some conditions, e.g. at test temperatures of 100° C. and above, this heat may cause the temperature of the block, and of the test fluid, to overshoot the intended level as set on the indicator-controller 44. When this occurs, or at other times if desired, the air pump 46 may be operated and the value 47 regulated to circulate air through the stator housing 27 in contact with the stator block and the heating coil. By careful regulation of the air flow, say at a few cubic feet per hour, the action of the heating coil may be tempered and the intended test temperature held accurately. Localized hot spots on the stator are avoided and heating and cooling take place both by conduction and convection.

While all rotational viscometers work best on test fluids which are clean, i.e. free of particulate matter, the instrument of the invention may be adapted to tolerate particles to a greater degree than prior instruments. The filter cartridge 35 will exclude particles larger than the fineness of its screen 34. However, when the rotor-stator gap is adjusted to narrower gaps, as is preferred for high shear rate measurement, particles small enough to pass the screen could none the less cause the test cell to jam, particularly with a rotor having simple flats. When such particles are present in a test fluid, the instrument may be readily opened by the handwheel 65 to increase the test cell gap, say to 10 microns, and measurements made at this value.

Figure 12:
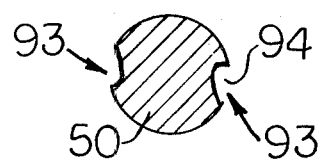
FIG. 12 is a horizontal section through the drum section of an alternate form of rotor, showing the filleted modified flats.

Another option for accommodating minute particles involves use of a special rotor shown in FIG. 12. In this design, the drum 50 is provided with special surfaces 93 which replace the conventional flats 53 (FIG. 6) with incised areas. The surfaces 93 in FIG. 12, herein called "incised areas", serve the same function as flats and resemble them in that they extend the full axial length of the rotor drum and are radially symmetrical and parallel to the rotor axis. The surfaces 93 are, however, not planar like a true flat, but are slightly cut away or depressed toward the axis of the rotor. In one version of an incised area shown in cross-section (FIG. 12) the face recedes gradually inward most of its width and returns sharply outward over the last part of its width back to the full diameter of the drum. This configuration provides the incised area with a narrow flute, notch, or fillet 94 constituting a pocket-like depression along its trailing edge. The depth of the fillet is small relative to the radius of the drum, preferably only one or two millimeters. The fillet 94 provides a slight groove or relief in which any particles in the test fluid may gather as the rotor turns; they are swept out when the test fluid is replaced. With the incised areas 93 the instrument may be operated on test fluids containing a significant amount of minute particles without jamming, even at a test cell gap of one to three microns.

With the instrument described, both the flat 53, and alternatively also the incised areas 93, serve the additional purpose of providing scrubbing action between the closely adjacent surfaces of the stator and rotor as the latter turns. This action quickly effects a complete exchange of fluid in the gap each time a new test sample is injected through the fill tube 33. Samples of fluid may thus be subjected to viscometric testing consecutively without the need to stop rotation and disassemble the instrument for cleaning between tests as has been the case with prior instruments. Rapidity of measurement of successive samples is greatly enhanced.

In the invention, with both the standard and modified rotors described, further advantage may be realized by providing a special degree of parallelism to the matching surfaces of the stator bore and rotor. Heretofore, in making tapered rotor/stator viscometers, especially those intended to operate with test gaps of only a few microns width, it has been customary to strive for close interfit of the stator bore and rotor by lapping them together, as with metal polish. Unfortunately, lapping does not provide mating surfaces which are truly parallel in the micro sense, in that lapping tends to introduce microgrooves into the surfaces. Thus, lapped surfaces which mate together with great precision at one axial position of the rotor may be a poor fit when the rotor is moved axially a few microns relative to the stator. In the present invention, this difficulty is avoided by separately machining the surfaces of the stator bore and of the rotor to reasonably close matching conical configuration. Thereafter each surface is separately subjected to a precision frustoconical grinding operation of the same alignment thereby producing closely matched parallel surfaces.

By virtue of its construction, the viscometer of the invention, especially when the rotor is fitted with the incised areas 93, is not limited to measuring and comparing the properties of lubricating oils. It may also be applied in rheological studies of solutions and suspensions, e.g. printer's inks, blood, liquid medicines, thin lacquers and latexes, and other fluids. In industrial processing, the instrument may be installed to monitor a stream of fluid continuously, even to provide on-line viscosity control. Viscosity range is at least 0.2 to 100 centipoises, depending on the maximum torque capable of being generated by the motor.

A special feature of the new viscometer is that the multispeed synchronous motor readily allows the rotor to be run at invariant speeds over wide ranges of torque. Compared to existing viscometers, the new instrument easily and quickly allows making comparison viscosity measurements of non-Newtonian liquids at different shear rates simply by taking readings at both motor speeds without otherwise adjusting the instrument. This feature is especially valuable to determining the lubrication effects of different non-Newtonian multigrade motor oils at shear rates or stresses approximating those of the automobile engine.

The new viscometer operates well at elevated temperatures in the range of 100° to 200° C., where it simulates the environment of lubricating oils in automotive engines. However, because of the ready adjustability of its clearances and the flexible system of temperature control, it may be used at room temperature. It may also be operated at low temperatures, e.g. below 0° C., to simulate the behavior of motor oils under winter cranking conditions, by circulating a chilling fluid at controlled temperature through the stator housing.

Another novel feature of the preferred form of the viscometer is that the motor platform 60 has only a single support, being cantilevered from the elevator mechanism. For most rotor/stator pairs this cantilever construction minimizes unwanted vibrations arising from the turning of the motor and rotor and renders the instrument unusually stable in regard to its torque readout.

In using the instrument with a rotor/stator pair having dimensions resulting in a different vibrational balance from that of the preferred form above, stability against vibration may be maximized by supporting the motor platform 60 not only at the elevator but also at its other end. This is done (after the rotor-stator gap is set) by adjusting the stop collars 67 on the shaft 66 to bear against the platform 60, locking it firmly in place. A third alternative, not illustrated, is to fit a slide bearing between the platform 60 and the shaft 66, so that the platform remains free to move up and down on its elevator but also receives substantial support from the shaft.

The pre-load assembly 80 has usefulness in addition to calibrating the load cell 86. For some measurements it is advantageous to apply a steady measured torque, in addition to that of the test cell, to the turntable 76. This extra load, applied by the cord 82 and weights 85 in known measured amount, adds sensitivity and stability in certain operating ranges.

The instrument of the invention is relatively simple and inexpensive to make, sturdy, and rapidly responsive to intended changes in temperature and other operating parameters. It is especially rapid in steadying out its readings after changing from one test fluid to another. It is flexible over wide ranges of temperature and viscosity, sensitive, and yet reliable in the hands of persons of limited experience.

I claim as my invention:

1. An elevated temperature variable-gap rotational viscometer comprising
    a thermally-conductive stator block embedded in thermal insulation and having an inverted frustoconical vertical bore, an inlet passage for admitting sample liquid axially into the bore at its bottom, and an overflow passage for sample liquid to leave the bore at its upper end;
    a thermal sensor recessed in the block;
    an element for heating the block responsive to the sensor;
    a matching rotor extending axially downward into the stator bore to define therebetween a thin annular measuring gap, the rotor having a flexible drive shaft extending axially upward from it;
    a multi-speed synchronous AC motor coaxial with and directly driving the shaft;
    a turntable fixed to and supporting the motor and having a torque arm projecting therefrom,
    the turntable being supported on a low-friction bearing resting on a cantilevered platform vertically adjustable by a fine screw, and being restricted in rotation to a limited arc; and
    a stationary force-measuring element opposing movement of the torque arm.

2. A viscometer according to claim 1 wherein the sensor-responsive heating element is an electric resistance heater encircling the stator block in a recess in the thermal insulation, the recess also being provided with means for passing a regulated stream of cooling fluid through it.

3. A viscometer according to claim 1 having a micrometer positioned to indicate the vertical position of the adjustable platform.

4. A viscometer according to claim 1 in which the matching surfaces of the stator and rotor defining the measuring gap are each separately ground to have closely parallel surfaces.

5. A viscometer according to claim 1 in which the force-measuring element is an electronic strain gage.

6. A viscometer according to claim 1 having pre-load means for applying a predetermined constant torque to the turntable in a direction opposite to that in which the motor turns.

7. A viscometer according to claim 1 wherein the matching surface of the rotor has symmetrically therein incised areas the surfaces of which have axially-extending shallow fillets.

8. A variable-gap rotational viscometer comprising a stator block having a frustoconical vertical sample-receiving bore;
    a matching rotor extending axially into the bore to define therebetween a thin annular measuring gap, the rotor having a drive shaft extending axially upward from it;
    a motor coaxial with and directly driving the shaft;
    a turntable fixed to and supporting the motor and free to rotate over a limited arc,
    the turntable being supported on a low-friction bearing resting on a platform vertically adjustable by an elevator mechanism; and
    means for restraining the rotation of the turntable and indicating the torque required to effect such restraint.

9. A viscometer according to claim 8 in which a micrometer is positioned to indicate the vertical position of the adjustable platform.

10. A viscometer according to claim 8 in which the elevator adjustment mechanism includes a fine screw.

11. A viscometer according to claim 8 in which a micrometer is positioned to indicate the vertical position of the adjustable platform.

12. A viscometer according to claim 8 having pre-load means for applying a predetermined constant torque to the turntable in the direction opposite to that in which the motor turns.

13. A viscometer according to claim 8 wherein the motor is a multi-speed synchronous AC motor.

14. In a rotational viscometer having a stator block with a sample-receiving bore and a matching rotor extending axially into the bore to define therebetween a thin annular measuring gap, the improvement in the rotor to gather any particles in the test fluid likely to jam in the gap consisting in that
    the matching surface of the rotor has therein incised areas radially symmetrical and extending the full axial length of the rotor, each incised area having axially therein a fillet constituting a pocket-like depression along its trailing edge to entrap particles, the depth of the fillet being small relative to the radius of the rotor.

15. A viscometer according to claim 14 in which each incised area is parallel to the rotor axis and the face of each fillet in the rotor recedes gradually inward most of its width and returns sharply outward over the last part of its width to the full diameter of the rotor.

* * * * *

UNITED STATES PATENT AND TRADEMARK OFFICE
CERTIFICATE OF CORRECTION

PATENT NO. : 4,445,365
DATED : May 1, 1984
INVENTOR(S) : Theodore W. Selby

It is certified that error appears in the above-identified patent and that said Letters Patent is hereby corrected as shown below:

Column 10, line 34, claim 11, change "8" to --10--.

Signed and Sealed this

Twenty-first Day of August 1984

[SEAL]

Attest:

GERALD J. MOSSINGHOFF

Attesting Officer     Commissioner of Patents and Trademarks